United States Patent [19]

Stober et al.

[11] 4,278,615

[45] Jul. 14, 1981

[54] PROCESS FOR THE PRODUCTION OF AROMATIC PEROXYCARBOXYLIC ACIDS

[75] Inventors: Reinhard Stober, Gross-Krotzenburg; Rolf Wirthwein, Hanau, both of Fed. Rep. of Germany

[73] Assignees: Degussa Aktiengessellschaft, Frankfurt; Henkel KGaA, Henkelstrasse, both of Fed. Rep. of Germany

[21] Appl. No.: 88,053

[22] Filed: Oct. 24, 1979

[30] Foreign Application Priority Data

Jul. 23, 1979 [DE] Fed. Rep. of Germany ....... 2929839

[51] Int. Cl.$^3$ ........................................... C07C 179/10
[52] U.S. Cl. .............................................. 260/502 R
[58] Field of Search ......................... 260/502 R, 502 A

[56] References Cited

U.S. PATENT DOCUMENTS

| | | | |
|---|---|---|---|
| 2,813,896 | 11/1957 | Krimm | 260/502 R |
| 3,143,562 | 8/1964 | Silbert et al. | 260/502 R |
| 3,284,491 | 11/1966 | Korach et al. | 260/502 R |
| 3,655,738 | 4/1972 | Nielsen | 260/502 R |
| 3,880,914 | 4/1975 | Nielsen | 260/502 R |
| 4,013,581 | 3/1977 | Huber | 252/186 R |
| 4,147,720 | 4/1979 | Berkowitz | 260/502 R |
| 4,147,729 | 4/1979 | Zupancic et al. | 260/502 R |

FOREIGN PATENT DOCUMENTS

| | | | |
|---|---|---|---|
| 1048569 | 1/1959 | Fed. Rep. of Germany | 260/502 R |
| 1155113 | 10/1963 | Fed. Rep. of Germany | 260/502 R |
| 930056 | 7/1963 | United Kingdom | 260/502 R |

OTHER PUBLICATIONS

Parker et al., "J. Amer. Chem. Soc." vol. 77 (1955) pp. 4037–4041.
Parker et al., "J. Amer. Chem. Soc." vol. 79 (1957) pp. 1929–1931.
Silbert et al., "Organ. Chem." vol. 27 (1962), pp. 1336–1342.
Swern, "Chemical Reviews," vol. 45 (1949), pp. 5–8.
Methodicum Chimicum, vol. 5 (1975), pp. 723–762, Academic Press, N.Y.

*Primary Examiner*—Werren B. Lone
*Attorney, Agent, or Firm*—Cushman, Darby & Cushman

[57] ABSTRACT

Aromatic peroxycarboxylic acids are produced by reacting aromatic carboxylic acids with hydrogen peroxide in the presence of sulfuric acid by having a mixture of aqueous 50–99 weight % $H_2O_2$ and sulfuric acid present in the reaction vessel, introducing the solid aromatic carboxylic acid with stirring, the reaction being carried out in heterogeneous phase, the stirring being continued to the end of the reaction and then the reaction mixture obtained worked up in known manner.

21 Claims, No Drawings

PROCESS FOR THE PRODUCTION OF AROMATIC PEROXYCARBOXYLIC ACIDS

BACKGROUND OF THE INVENTION

For a long time it has been known that aliphatic peroxycarboxylic acids (aliphatic percarboxylic acids) can be produced by reaction of the aliphatic carboxylic acid in question with hydrogen peroxide in the presence of sulfuric acid, see, e.g., Swern, Chemical Reviews, Vol. 45 (1949) page 5; Silbert, et al, J. Org. Chem. Vol. 27 (1962), pages 1336-1342.

While this process is successful for obtaining aliphatic peroxycarboxylic acids, repeated attempts to use it for the reaction of aromatic acids with hydrogen peroxide did not lead to the desired results. Either there resulted decarboxylation or sulfonation/hydroxylation of the aromatic ring or total oxidative decomposition, see Silbert, et al, loc. cit. page 1337; Silbert U.S. Pat. No. 3,143,562 and related Swern German AS 1155113 as well as related Koninklijke British Pat. No. 930,056, Melthodicum Vol. 5 (1975) C-O-Verbindungen, page 739; Berkowitz U.S. Pat. No. 4,147,720.

Those skilled in the art until recent times were under the impression that sulfuric acid was unsuited as a solvent or even only as a catalyst acid for the production of aromatic peroxycarboxylic acids (aromatic percarboxylic acids).

In order to meet these difficulties the system "aromatic carboxylic acid-hydrogen peroxide-sulfuric acid" was replaced by the system "aromatic acid-hydrogen peroxide-methanesulfonic acid", i.e. in place of sulfuric acid there was used methanesulfonic acid, see Silbert, loc. cit.

However, in contrast to sulfuric acid, methane sulfonic acid is not an easily accessible industrial based chemical and thereby places an unlimited burden for carrying out the process industrially.

Since the aromatic percarboxylic acids also are included in the important oxidizing agents and e.g. play a roll in epoxidation and also in the oxidation of sulfides or tert. amines as well as bleaching and disinfecting agents, it has been very strongly desired to have a process which permits the production of aromatic percarboxylic acids without the use of industrially very expensive materials.

The purpose of the invention therefore is the development of a process for the production of aromatic percarboxylic acids using readily available industrial materials.

SUMMARY OF THE INVENTION

It has now been found that aromatic percarboxylic acids can be produced by reacting the carboxylic acid in question with hydrogen peroxide in the presence of sulfuric acid by having a mixture of aqueous 50-99 weight % $H_2O_2$ and sulfuric acid present in the reaction vessel, introducing the solid aromatic carboxylic acid with stirring, the reaction being carried out in heterogeneous phase, the stirring being continued to the end of the reaction and then the reaction mixture obtained being worked up in known manner.

As aromatic carboxylic acids there can be used both monobasic and polybasic, preferably dibasic carboxylic acids such as benzoic acid, the phthalic acids, as well as benzene di and polycarboxylic acids and their derivatives of the formula

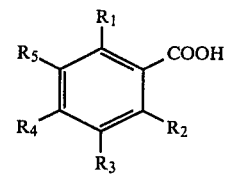

wherein $R_1$, $R_2$, $R_3$, $R_4$ and $R_5$ are hydrogen, COOH, 1-4 carbon atom alkyl, 1-4 carbon atom alkoxy and/or halogen e.g. chlorine, fluorine or bromine.

The carboxylic acids including those with other substituents can also be added as mixtures.

Examples of aromatic carboxylic acids are benzoic acid, o-phthalic acid, isophthalic acid, terephthalic acid, mellitic acid, hemimellitic acid, trimellitic acid, trimesic acid, prehnitic acid, pyromellitic acid, benzenepentacarboxylic acid, o- toluic acid, m-toluic acid, p-toluic acid, o-chlorobenzoic acid, p-chlorobenzoic acid, m-chlorobenzoic acid, p-bromobenzoic acid, o-fluorobenzoic acid, o-fluorobenzoic acid, 2,4-dichlorobenzoic acid, 2-methyl-4-chlorobenzoic acid, p-ethyl benzoic acid, p-butyl benzoic acid, p-t-butyl benzoic acid, 1-methoxy benzoic acid, p-butoxy benzoic acid, o-ethoxy benzoic acid, 1-methyl-2,4-dicarboxybenzene and 2,4-dimethyl benzoic acid.

Since the aromatic carboxylic acids at room temperature are present in solid form the process of the invention takes place in heterogeneous phase. Special particle sizes of the aromatic carboxylic acids are not necessary for the process. However, the smaller the particle size of the added aromatic polycarboxylic acid the better the reaction runs. Preferably the particle size of the aromatic carboxylic acid not over 0.2 mm.

The hydrogen peroxide is preferably used in concentrations of 70 to 85 weight %, the sulfuric acid in concentrations of 50 to 100 weight %, preferably of 96 weight %.

The mol ratio of hydrogen peroxide to sulfuric acid in the proposed mixture varies from 1:0.67 to 2:1. The addition of more hydrogen peroxide does not lead to any mentionable increase in yield.

The aromatic carboxylic acids are added to the mixture in solid form, preferably pulverized.

The mol ratio "carboxylic acid" to hydrogen peroxide to sulfuric acid is between 1:2:3 to 1:1:10. It is adjustable at random within these values. Here also for higher mol ratios there are only insignificant higher yields.

The reaction occurs at a starting temperature from 20° to 70° C., preferably at 40°-60° C. The introduction of the carboxylic acid can take place by hand or through customary dosing devices.

The duration of the introduction depends both on the type of reaction established, i.e. whether stronger or weaker, on the particle size of the aromatic carboxylic acid, i.e. the smaller, the quicker and on the liberated heat of reaction. Thereby the respective mol ratios of carboxylic acid to hydrogen peroxide to sulfuric acid plays a role.

The smaller is the heat of reaction or the higher the above defined mole ratio, the more quickly is the introduction completed.

Thus, e.g., in producing diperoxyisophthalic acid (diperisophthalic acid) using a mole ratio of isophthalic acid to hydrogen peroxide to sulfuric acid of 1:5:5 a few minutes is sufficient for adding the solid carboxylic acid. The heat of reaction in this case is negligibly small, on the contrary for complete reaction it is necessary to heat the reaction mixture.

By "stirring" there is preferably meant a turbulent thorough mixing.

The working up of the reaction mixture can be carried out in known manner, e.g., according to Nielsen U.S. Pat. Nos. 3,880,914 and 3,655,738 and Parker et al J. Amer. Chem. Soc. Vol. 77(1955) pages 4037–4041 and Vol. 79(1957) pages 1929–1931; Gilbert et al. J. Org. Chem. Vol. 27 (1962) pages 1336–1342 and Berkowitz U.S. Pat. No. 4,147,720.

The process of the invention is particularly well suited for the production of benzene diperoxy carboxylic acids (diperoxyphthalic acids).

According to the process of the invention the aromatic percarboxylic acids are generally obtained in yields of 10 to 80 weight % with a peroxy acid content of 5 to 90 weight%, Even yields of 10 weight % with many aromatic peroxycarboxylic acids means a considerable increase, since e.g. diperoxyterephthalic acid even with the use of methanesulfonic acid was only obtained in yields below 5 weight %. In contract according to the process of the invention it is obtained in a yield of 14 weight %. For comparison German AS No. 1,155,113 in Example 18A shows a yield of diperoxyterphthalic acid of less than 5% starting from terephthalic acid.

Of course according the process of German AS 1048569 or related Krimm U.S. Pat. No. 2,813,896 it is known to produce peroxycarboxylic acids and even aromatic peroxycarboxylic acids in the presence of sulfuric acid. However, emphasis is expressly made of the fact that the reaction is carried out in homogeneous solution. Therefore, e.g., peroxybenzoic acid is produced in an aqueous-ether solution, a process which is hazardous from an industrial safety view point and besides which it is very time consuming.

Likewise a strong aqueous mixture of 35 weight % hydrogen peroxide and 95–98 weight % sulfuric acid as is used in Huber U.S. Pat. No. 4,013,581 for the production of diperazelaic acid has proven completely unsuitable for the production of aromatic percarboxylic acids. There does not occur a reaction to the desired percarboxylic acid.

Concentrated solutions with e.g., 50 weight % of hydrogen peroxide according to Gilbert, Siegel and Swern, J. Org. Chem. Vol. 27(1962), pages 1336–1342 lead to decomposition of the added aromatic carboxylic acids.

Thus even until the most recent time there have been warnings against the use of sulfuric acid for the production of aromatic percarboxylic acids (see loc. cit. Methodicum Chemicum and Berkowitz U.S. Pat. No. 4,147,720). Instead there were considered as necessary special conditions even using methanesulfonic acid, as e.g., special particle sizes of the phthalic acids employed, see Nielsen, U.S. Pat. No. 3,655,738.

Thus it is very surprising that contrary to the view of those skilled in the art there was a possibility of producing aromatic percarboxylic acids, preferably aromatic perdicarboxylic acids, in good yields and with high peroxycarboxylic acid content, in a simple manner industrially with the system "aromatic carboxylic acid-hydrogen peroxidesulfuric acid".

Unless otherwise indicated all parts and percentages are by weight. The process can comprise, consist essentially of or consist of the steps set forth employing the materials set forth.

The invention will be described in connection with the following examples.

DESCRIPTION OF THE PREFERRED EMBODIMENTS

EXAMPLE 1

Diperoxyphthalic Acid (DPP)

There were added 17 grams of pulverized phthalic acid (o-phthalic acid) with stirring at 20° C. within 10 minutes to a mixture of 51 grams of 96% $H_2SO_4$ (0.5 mole) and 28.4 grams of 60 weight % $H_2O_2$ (0.5 mole, the reaction mixture heated to 40° C. and stirred at this temperature for 6 hours. After cooling to 10°–15° C. there were added 150 ml of saturated $(NH_4)_2SO_4$ solution, the reaction mixture filtered and the residue rewashed with ice water. Drying of the filtered residue produced 15.5 grams of product having a content of diperoxyphthalic acid of 49.3% (measured iodometrically) corresponding to a yield of 38.4%.

EXAMPLE 2

Diperoxyisophthalic acid (DPIP)

General Procedure

Pulverized isophthalic acid was added with stirring to a mixture of $H_2O_2$ and $H_2SO_4$ within 20 minutes and stirred at the reaction temperature in each case for 2–40 hours. After cooling to 0°–10° C. there were added 200 ml of ice water, the reaction mixture filtered and the residue washed with ice water to a pH of 3–4. After drying the product there was obtained a product which in addition to diperoxyisophthalic acid only contained starting material (isophthalic acid).

The carrying out of the experiments which led to the result in Tables 1–4 are set forth in regard to the amounts of addition and reaction conditions for experiments 3 and 4 in Table 1.

| TO EXPERIMENT 3 | |
| --- | --- |
| Formulation: | 120 grams 85% $H_2O_2$ (3.0 moles) |
| | 306 grams 96% $H_2SO_2$ (3.0 moles) |
| | 99.7 grams isophthalic acid (0.6 mole) |
| Reaction temperature: | 50° C. |
| Reaction time: | 23 hours |
| yield: | 104 grams having a cent of DPIP of 88.7% corresponding to a yield of 77.5% |

| TO EXPERIMENT 4 | |
| --- | --- |
| Formulation: | 80 grams 58% $H_2O_2$ (2.0 moles) |
| | 204 grams 96% $H_2SO_2$ (2.0 moles) |
| | 66.4 grams Isophthalic acid (0.4 moles) |
| Reactions temperature: | 60° C. |
| Reaction time | 7.5 hours |
| Yield: | 64.2 grams having of content of DPIP of 72.3% corresponding to a yield of 58.6% |
| Elemental analysis | |
| found: | C: 51.02% H: 3.32% |
| calculated: | C: 51.09% H: 3.21% |
| (with 72.3% DPIP) | |
| Sulfur detection: | negative |
| Thin layer chromatogram: | two components |

(Running agent: tert.-Butanol/glacial acetic acid/$H_2O$ = 4 : 1 : 1)

-continued

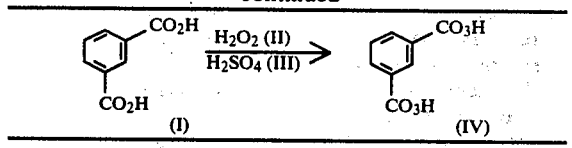

TABLE 1
Use of 85 wt. % $H_2O_2$
Mole Ratio I : II : III = 1 : 5 : 5

| | Reaction temp. °C. | Reaction time hours | DPIP-Content % | DPIP-Yield % |
|---|---|---|---|---|
| 1 | 60[a] | 2.2 | 60.8 | 46.7 |
| 2 | 60 | 7.5 | 72.3 | 59.0 |
| 3 | 50[b] | 7 | 80.0 | 67.0 |
| 4 | 50 | 23 | 88.7 | 77.5 |
| 5 | 40 | 23 | 83.2 | 73.5 |
| 6 | 40[b] | 39 | 85.5 | not determined[c] |
| 7 | 30 | 23 | 43.5 | 38.5 |

[a]short time at 71° C. [b]additional 16 h at room temperature [c]yield not determined, since mixture distributed multiply.

TABLE 2
Use of 85.0 Wt.-% $H_2O_2$
Various Mole Ratios

| Mole Ratios I:II:III | React.-Temp. °C. | React.-Time h | DPIP-Content % | DDIP-Yield % |
|---|---|---|---|---|
| 1:10:5 | 40 | 6 | 18.5 | 15.3 |
| 1:4:4 | 50 | 23 | 79.9 | 71.0 |
| 1:4:4 | 40 | 23 | 73.8 | 67.3 |
| 1:3:5 | 40 | 23 | 35.3 | 26.8 |
| 1:2.5:3 | 40 | 23 | 52.0 | 45.0 |
| 1:2:3 | 40 | 23 | 33.5 | 27.5 |

TABLE 3
Use of 70 Wt.-% $H_2O_2$
Mole Ratio I : II : III = 1 : 5 : 5

| React.-Temp. °C. | React. Time h | DPIP-Content % | DPIP-Yield % |
|---|---|---|---|
| 55 | 23 | 59.9 | 52.4 |
| 50 | 23 | 64.5 | 57.8 |
| 50[a] | 23 | 48.0 | 42.0 |
| 40 | 23 | 43.7 | 38.6 |

[a]Addition of 1-Hydroxyethane-1,1-diphosphonic acid (60Wt % aqueous solution)

TABLE 4
Use of 70.0 Wt.-% $H_2O_2$
Various Mole Ratios

| Mole Ratios I:II:III | React.-Temp. °C. | React.-Time h | DPIP-Content % | DIP-Yield % |
|---|---|---|---|---|
| 1:10:5 | 40 | 6 | 1.5 | 1.3 |
| 1:4:4 | 40 | 23 | 35.6 | 30.8 |
| 1:3:5 | 40 | 23 | 45.3 | 38.5 |
| 1:2.5:3 | 50 | 23 | 40.3 | 34.8 |
| 1:2:3 | 50 | 23 | 28.8 | 23.9 |

Diperoxyterephthalic Acid (DPTP)
General Procedure as In Example 2
Typical Example

| | |
|---|---|
| Formulation: | 20 grams 83% $H_2O_2$ (0.5 mole) |
| | 51 grams 96% $H_2SO_2$ (0.5 mole) |
| | 17 grams Terephthalic Acid (0.1 mole) |
| Reaction temperature: | 50° C. |
| Reaction time: | 23 hours |
| Yield: | 17 grams with a content of DPTP of 15.8% corresponding to a yield of 13.6%. |

The entire disclosure of German priority application P No. 2929839.3 is hereby incorporated by reference.

What is claimed is:

1. A process for the production of an aromatic peroxycarboxylic acid comprising introducing with stirring a solid aromatic carboxylic acid of the formula

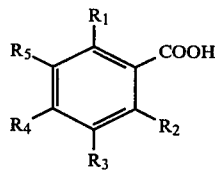

wherein $R_1$, $R_2$, $R_3$, $R_4$ and $R_5$ are hydrogen, COOH, 1-4 carbon atom alkyl, 1-4 carbon atom alkoxy or halogen into a mixture of aqueous 50-99 weight % hydrogen peroxide and sulfuric acid, carrying out the reaction of the aromatic acid with said mixture in heterogeneous phase and recovering the aromatic peroxycarboxylic acid formed, the reaction mixture consisting essentially of the solid aromatic carboxylic acid, water, hydrogen peroxide and sulfuric acid.

2. The process of claim 1 wherein the reaction mixture consists of the solid aromatic carboxylic acid, water, $H_2O_2$ and sulfuric acid.

3. The process of claim 1 wherein the aromatic carboxylic acid is a phthalic acid of the group consisting of o-phthalic acid, isophthalic acid and terephthalic acid.

4. The process of claim 3 wherein the phthalic acid is o-phthalic acid.

5. The process of claim 3 wherein the phthalic acid is isophthalic acid.

6. The process of claim 3 wherein the phthalic acid is terephthalic acid.

7. The process of claim 3 wherein the mole ratio of hydrogen peroxide to sulfuric acid is from 0.67 to 2:1.

8. The process of claim 7 wherein the mole ratio of phthalic acid to hydrogen peroxide to sulfuric acid is from 1:2:3 to 1:10:10.

9. The process of claim 8 wherein the reaction is started at a temperature of 40°-60° C.

10. The process of claim 8 wherein the reaction mixture consists of the solid aromatic carboxylic acid, water, hydrogen peroxide and sulfuric acid.

11. The process of claim 1 wherein the mole ratio of hydrogen peroxide to sulfuric acids is from 0.67 to 2:1.

12. The process of claim 11 wherein the mole ratio of solid aromatic carboxylic acid to hydrogen peroxide to sulfuric acid is from 1:2:3 to 1:10:10.

13. The process of claim 12 wherein the reaction is started at a temperature of 40°–60° C.

14. The process of claim 1 wherein the reaction is started at a temperature of 40°–60° C.

15. The process of claim 1 wherein the solid aromatic carboxylic acid is employed in pulverized condition.

16. The process of claim 1 wherein the starting temperature is 20° to 70° C.

17. The process of claim 1 wherein the starting temperature is 20° to 70° C.

18. The process of claim 2 wherein the starting temperature is 20° to 70° C.

19. The process of claim 3 wherein the starting tempeature is 20° to 70° C.

20. The process of claim 8 wherein the starting temperature is 20° to 70° C.

21. The process of claim 15 wherein the starting temperature is 20° to 70° C.

* * * * *